United States Patent [19]
Rabinovitz et al.

[11] Patent Number: 5,545,639
[45] Date of Patent: Aug. 13, 1996

[54] METHOD OF INHIBITING TRANSFORMED CELLS

[75] Inventors: Marco Rabinovitz; Joyce M. Fisher, both of Bethesda, Md.

[73] Assignee: The United States of America as represented by the Department of Health and Human Services, Washington, D.C.

[21] Appl. No.: 198,953

[22] Filed: Feb. 18, 1994

[51] Int. Cl.[6] .................................................. A61K 31/44
[52] U.S. Cl. ............................................................ 514/292
[58] Field of Search ............................................. 514/292

[56] References Cited

U.S. PATENT DOCUMENTS 2,617,753  11/1952  Gysin et al. ............................ 514/292

OTHER PUBLICATIONS

Albert, "Metal–binding substances," in *Selective Toxicity*, 7th ed., Chapter 11, 430–489 (1981).
Berger et al., "Othro–Phenanthroline Inhibition of DNA Synthesis in Mammalian Cells," *Exp. Cell Res.*, 96, 145–155(1975).
Blank, "*In vitro* fungistatic action of phenanthrolines against pathogenic fungi," *Nature*, 168, 516–517 (1951).
Bridgland et al., "N–oxide complexes of vanadium(IV) chloride, " *J. Inorg. Nucl. Chem.*, 31, 43–48 (1969).
Chassapis et al., "Chelates of the Rare Earth Notrates with 1,10–Phenanthroline–N,N'–Dioxide," *Inorganica Chimica Acta*, 27, 67–68 (1978).
Falchuk et al., "1,10–Phenanthroline Inhibition of Lymphoblast Cell Cycle," *Cancer Res.*, 37, 2050–2056 (1977).
Mathes et al., "(Halogenomethyl)pyridines and (Halogenomethyl)quinolines,"*Angew. Chem Internat. Ed.*, 2, 144–149 (1963).
Mohindru et al., "2,9–Dimethyl–1,10–Phenanthroline (neocuproine): A Potent, Copper–Dependent Cytotoxin with Anti–Tumor Activity," *Biochem. Pharmacol.*, 32, 3627–3632 (1983).

Newkome et al., "Mono–α–functionalization of 2,9–Dimethyl–1,10–Phenanthroline," *J. Org. Chem.*, 54, 1766–1769 (1989).
Newkome et al., "α–Methyl Functionalization of Electron––Poor Heterocycles: 2,9–Bis(chloromethyl)–1,10–phenanthroline. Synthesis of a [3,3]Cyclophane Containing the 1,10–Phenanthroline Moiety," *J. Org. Chem.*, 48, 5112–5114 (1983).
Shulman et al., "Action of 1, 10–Phenanthroline Transition Metal Chelates of P388 Mouse Lymphocytic Leukaemic Cells," *Chem.–Biol. Interactions*, 16, 89–99 (1977).
Shulman et al., "Virostatic Activity of 1,10–Phenanthroline Transition Metal Chelates: A Structure–Activity Analysis," *Chem. Biol. Interactions*, 6, 407–413 (1973).
Shulman et al., "The Lethal Action of 1,10–Phenanthroline Transition Metal Chelates and Related Compounds on Dermatophytes and *Candida albicans*," *Arzneim.–Forsch. (Drug Res.)*, 22,, 154–158 (1972).
Shulman et al., "Metal Chelates in Biological Systems," in *Chelating Agents and Metal Agents*, Dwyer et al., eds., Chapter 9, 383–439 (Academic Press, New York, NY, 1964).
Sliwa, "1,10–Phanenthroline and its Complexes," *Heterocycles*, 12, 1207–1237 (1979).
Toissel, "Table of Intravenous Infusion Solutions," *ASHP Handbook on Injectable Drugs*, 4th ed., 622–630 (1986).
Butler et al., "Bactericidal action of selected phenthroline chelates and related compounds," *Aust. J. Exp. Biol. Med. Sci.*, 47, 541–552 (1969).

*Primary Examiner*—Jerome D. Goldberg
*Attorney, Agent, or Firm*—Leydig, Voit & Mayer, Ltd.

[57] ABSTRACT

The present invention relates to a method for the inhibition of transformed cells, comprising the application of an effective amount of at least one of the group consisting of 2,9-bis(halomethyl)-1,10-phenanthroline and structural congeners thereof.

27 Claims, 3 Drawing Sheets

METHOD OF INHIBITING TRANSFORMED CELLS

FIELD OF THE INVENTION

The present invention relates to the use of compounds capable of selectively inhibiting transformed cells. The present invention is related in particular to a method of inhibiting transformed cells that has little or no effect on nontransformed cells.

BACKGROUND OF THE INVENTION

Cell division is ordinarily controlled in multicellular organisms such that cells grow within certain bounds, at certain rates, and adjacent to certain other cells. Cells derived from such organisms exhibit such controlled growth even when placed in culture. Thus, for example, these cells will grow in a petri dish until a certain density of cells occupies the dish, thereafter attaining a quiescent, non-dividing or very slow dividing stage. This characteristic of normal cells is a function of some combination of cellular contact and the concentration of a factor or factors that accumulates in the medium in which the cells are plated. Other properties of normal cells include: oriented growth, lack of fetal or virus-specific antigens on the cell surface, high serum requirement for growth, inability to grow in agar, and inability to cause tumor formation upon injection into susceptible animals.

However, within any given culture, and within any given multicellular organism, a proportion of the cells will lose their characteristic of controlled growth, and proliferate to excess. Such cells are referred to as "transformed," which cells may grow in culture to saturation densities that are 10–25 times greater than those of nontransformed normal cells, when nutritional factors probably become limiting. Transformation can be induced using any of various agents, including certain viruses and chemicals. Transformation may also be an inherent property of normal cells, such that at some rate, all cells will transform. Transformed cells include tumor or cancer cells, whether in vivo or in vitro, such as cells from non-small cell lung cancer, small cell lung cancer, colon cancer, melanoma, ovarian cancer, and renal cancer.

Agents that specifically, preferentially, or predominantly inhibit or stop the growth of transformed cells have utility for the negative selection of transformed cells as well as for use in chemotherapy for various forms of cancer. Thus, whether in vivo or in vitro, transformed cells exhibiting uncontrolled growth would be inhibited or killed by such agents, while allowing the generally slower growing non-transformed, normal cells to survive unfettered (or less fettered) by the transformed cells. Such agents generically are classified as cytotoxins, among which are alkylating agents.

The cytotoxic agent 2,9-dimethyl-1,10-phenanthroline ("2,9-DMP") is a potent, copper dependent cytotoxin, whose administration as a chemotherapeutic agent is limited by its neurotoxic characteristic. The coordinated copper complex of 2,9-DMP has been shown to be effective in tissue culture at nanomolar concentrations for the killing of mouse L1210 cells, for example, which is an established murine lymphoma line. When L1210 cells were implanted into a susceptible animal, and a tumor began growing therefrom, the observed inhibitory responses were evident, although weak, when the L1210-implanted animals received 2,9-DMP with copper. Mice inoculated with P388 murine lymphocytic leukemia cells, however, responded well to such 2,9-DMP treatment, resulting in 45% increases in life span in the treated group. Despite the positive result with the P388 cells, however, 2,9-DMP is not considered a good candidate for widespread use because it is a known neurotoxin. See Mohindru et al., *Biochem. Pharmacol.*, 32, 3627–3632 (1983).

The parent compound to 2,9-DMP is 1,10-phenanthroline ("phenanthroline"), which also has cytotoxic capabilities. Phenanthroline has known antibacterial, antifungal, antiviral, and antineoplastic characteristics. See Blank, *Nature*, 168, 516–517 (1951); Butler et al., *Aust. J. Exp. Biol.*, 47, 541 (1969); Shulman et al., *Arzneimittel-Forsch*, 22, 154 (1972); Shulman et al., *Chem. Biol. Interact.*, 6 407 (1973); Shulman et al., *Chem. Biol. Interact.*, 16, 89 (1977). Its cytotoxic characteristic is believed to be a function of its ability to chelate various divalent metal ions, such as zinc, which would thereby inhibit, for example, zinc-dependent nucleotidyl transferases and DNA synthesis. In each of the systems studied whereby the various cytotoxic effects have been observed, the addition of divalent metal ions has reversed the toxic effect. See Berger et al., *Exp. Cell Res.*, 96, 145 (1975); Falchuk et al., *Cancer Res.*, 37, 2050 (1977). However, various alkylated derivatives of phenanthroline complexed with any of the divalent metal ions $Cu^{++}$, $Co^{++}$, $Fe^{++}$, $Zn^{++}$, and $Ru^{++}$ have been reported to be cytotoxic, albeit the degree of toxicity was seen to vary from 100% kill down to only 6% kill in 6 hours incubation (Shulman 1977, supra). In none of the studies, thus far, has a cytotoxic alkylating compound been identified that selectively inhibits transformed cells while leaving normal ones unaffected or affected in a limited or minor way.

There remains a need, therefore, for a compound that allows for the selection of nontransformed cells by inhibiting the growth of transformed cells. Such a compound preferably would be toxic to transformed cells while having little or no toxic effects on nontransformed cells. The present invention provides a compound and its method of use, which method allows for such a selection of nontransformed cells. These and other objects and advantages of the present invention, as well as additional inventive features, will be apparent from the description of the invention provided herein.

SUMMARY OF THE INVENTION

The present invention provides a method of inhibiting transformed cells, which method comprises contacting transformed cells with certain phenanthroline derivatives that contain halomethyl groups adjacent to heterocyclic nitrogen atoms. The generic formula for the active agent used in the method is 2,9-bis(halomethyl)-1,10-phenanthroline; the bromine and chlorine species are preferred. Pharmaceutical compositions comprising the active agent are also provided by the present invention.

DETAILED DESCRIPTION OF THE INVENTION

Figure 1:
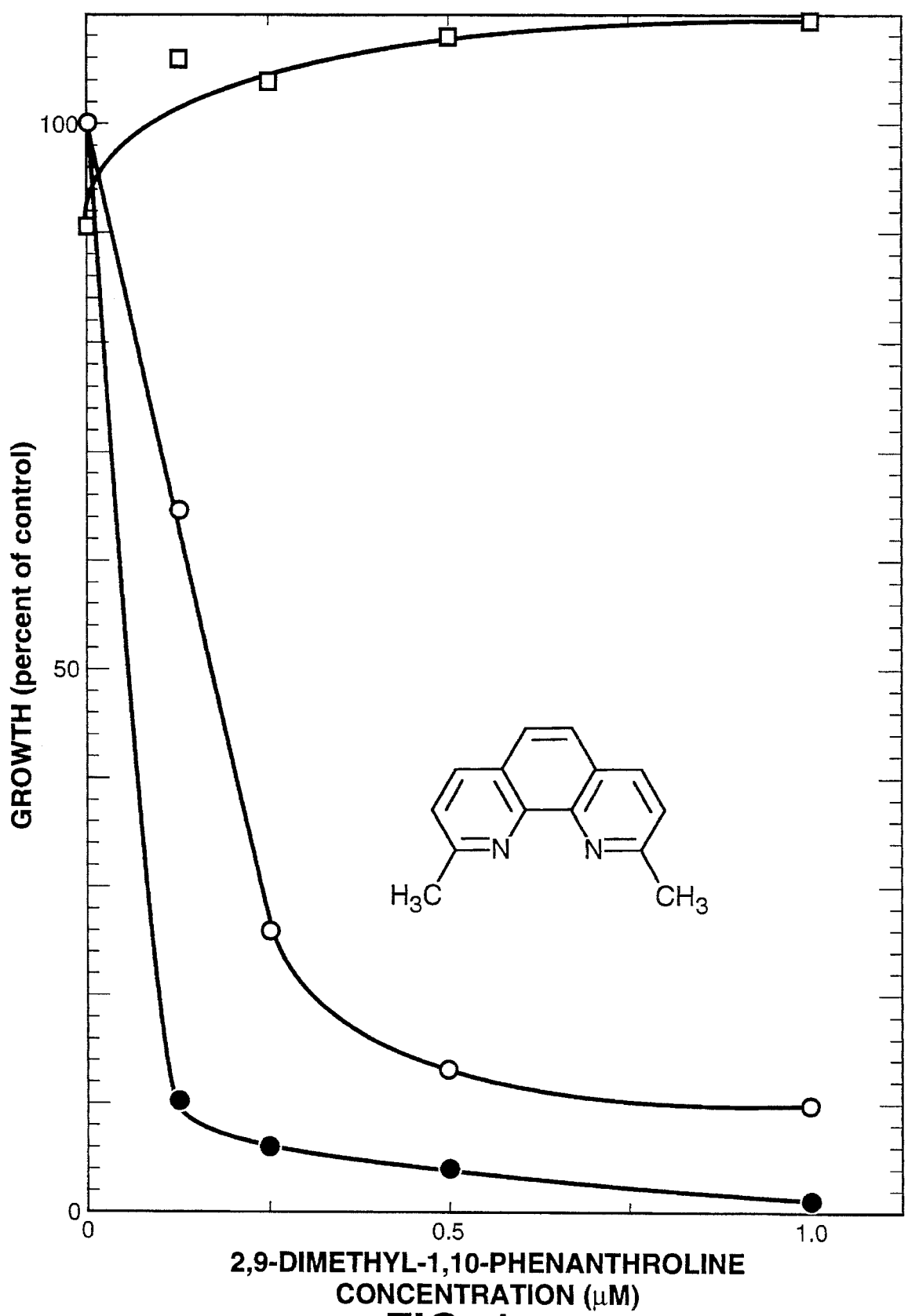
FIG. 1 is a graph that illustrates the inhibition of growth of murine L1210 leukemia cells in culture when incubated in the presence of varying concentrations of (1) 2,9-dimethyl-1,10-phenanthroline with copper (●); (2) 2,9-dimethyl-1,10-phenanthroline alone (o); and (3) 2,9-dimethyl-1,10-phenanthroline with copper and bathocuproine disulfonate (□).

The present invention provides a method for the inhibition of transformed cells thereby allowing nontransformed cells to grow unimpeded by transformed cells. The nontransformed cells are unaffected or largely unaffected by the present inventive method, as indicated by the lack of toxicity in an animal. This method comprises the application of certain phenanthroline derivatives, which are alkylating agents, that contain halomethyl groups adjacent to heterocyclic nitrogen atoms, as illustrated in the following generic formula:

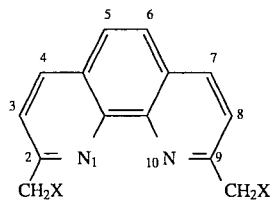

wherein X is bromo, chloro, iodo, or fluoro. Structural congeners of the phenanthroline derivatives of the formula are contemplated to be used in the present invention, either in addition to the chemical species of the formula or in place of the chemical species of the formula. Such congeners include, but are not limited to, compounds containing substituents at the 3, 4, 5, 6, 7 and/or 8 positions and/or substitutions for the hydrogens at the 2 and/or 9 positions. For example, representative congener species include 3,4,7,8-tetramethyl-2,9,-bis(chloromethyl)- 1,10-phenanthroline, 3,5,6,8-tetramethyl- 2,9-bis(chloromethyl)-1,10-phenanthroline, 5-methyl- 2,9-bis(chloromethyl)-1,10-phenanthroline, 4,7-dimethyl- 2,9-bis(chloromethyl)-1,10-phenanthroline, and 3,4,5,6,7,8-hexamethyl-2,9-bis(chloromethyl)-1,10-phenanthroline. In the present invention, the aforementioned phenanthroline derivatives and/or its congeners constitute the active ingredient or ingredients in a selective composition for the in vitro inhibition of transformed cells or in a pharmaceutical composition for the in vivo inhibition of transformed cells.

The in vitro inhibition of transformed cells concerns the negative selection of transformed cells in a cell culture, such that such cells are either destroyed, directly or indirectly, or hindered in their growth. Culturing concerns the incubation of explanted organs, tissues, and/or cells from animals, including humans and other mammals, in laboratory vessels, such as a petri dish or other culturing apparatus, with suitable culture media. The culture media may be undefined, complex media, such as those media that include fetal bovine serum or an extract of an organ as an integral component, or may be defined as to all chemical components. Both primary cultures of such explanted materials and secondary cultures of cell strains derived from such primary cultures appropriately may be cultured using the inventive method for the purpose of selecting against any transformed cells contained in the explanted tissue or resultant cell strain, or against any transformed cells that may arise in such culturing.

The in vivo inhibition of transformed cells concerns the negative selection of transformed cells in animals, including humans and other mammals, such that such cells are either destroyed, directly or indirectly, or hindered in their growth. Such a selection may be applied when, for example, a tissue is incubated in the peritoneum of an animal for purposes of growth and preservation of the tissue, which tissue may be grown only more inconveniently (or, perhaps, impossibly) using in vitro techniques. For example, it is known in the art that embryos of certain bovines have been literally transported in rabbits in this fashion. Such a selection may also be applied to animals, including humans and other mammals, whose tissues include spontaneously transformed cells, as in cancerous conditions. Such in vivo application of the present invention has been shown surprisingly to have associated with it a very low level of toxicity, as when applied to a mammal such as a mouse.

In particular, the present invention relates to a method of inhibiting transformed cells, which method comprises contacting the cells with an inhibiting concentration or amount of at least one compound of the group consisting of 2,9-bis(halomethyl)-1,10-phenanthroline and congeners thereof. The compound used in the present invention is preferably 2,9-bis(halomethyl)- 1,10-phenanthroline, more preferably 2,9-bis(bromomethyl)- 1,10-phenanthroline or 2,9-bis(chloromethyl)- 1,10-phenanthroline, and most preferably 2,9-bis(chloromethyl)-1,10-phenanthroline. Although the preferred embodiments of the present invention include the use of just one or two different active ingredients, it is contemplated that the invention may be practiced with a multiplicity of active ingredients.

An inhibiting concentration or amount is that quantity or range of quantities of the active ingredient that will inhibit, i.e., stop or impede, the growth of the transformed cells, preferably, but not necessarily, including the killing of such cells. For cells grown in vitro, the present invention is applied preferably in terms of an inhibiting concentration, such that the concentration of the active ingredient, such as, for example, the bis(chloromethyl) compound, in the culture medium is at least about 0.1 micromolar. More preferably, the concentration of the active ingredient used for cells grown in culture is from about 0.1 to about 10 micromolar. For in vivo cells in animals, including humans and other mammals, the present invention is applied preferably in terms of an inhibiting amount, such that the animal recipient is provided an amount that is at least about 0.1 mg per kg of body mass. More preferably, the amount of the active ingredient provided to the animal recipient is from about 0.1 mg per kg of body mass to about 1000 mg per kg of body mass. Most preferably, the amount of the active ingredient provided is from about 1 mg to about 500 mg per kg of body mass.

Generally, the ranges of active ingredient used in the present invention, as stated above, are correct as to the genus of 2,9-bis(halomethyl)-1,10-phenanthroline. Individual species may have more refined ranges. For example, when the compound used as the active ingredient is 2,9-bis(chloromethyl)-1,10-phenanthroline, the preferred minimum concentration applied to cells in vitro is about 1 micromolar, and the preferred minimum amount applied to cells in an animal is about 1 mg per kg of body mass; more preferably, the concentration applied to cells in vitro is from about 1 micromolar to about 800 micromolar, and the amount applied to cells in vivo is from about 1 mg to about 1000 mg per kg of body mass of the animal. For in vitro use, it is most preferred to apply a concentration of from about 2 micromolar to about 150 micromolar. For in vivo use, it is most preferred to apply from about 10 mg to about 500 mg per kg of body mass.

When the compound used as the active ingredient is 2,9-bis(bromomethyl)-1,10-phenanthroline, however, the preferred minimum concentration applied to cells in vitro is about 0.1 micromolar, and the preferred minimum amount applied to cells in an animal is about 0.1 mg per kg of body mass of the animal; more preferably, the concentration applied to cells in vitro is from about 0.1 micromolar to about 200 micromolar, and the amount applied to cells in vivo is from about 0.1 mg to about 50 mg per kg of body mass of the animal. For in vivo use, it is most preferred to apply from about 1 mg to about 40 mg per kg of body mass.

The present inventive method is useful in inhibiting the growth of a wide variety of transformed cells, such as, for example, transformed cells involved in lung, colon, ovary, skin, blood, central nervous system, and kidney tissues. Transformed cells derived from the aforementioned tissues have been shown to be susceptible to the active ingredient of the present invention. One skilled in the art may apply the present invention to the inhibition of other transformed cells without need to resort to undue experimentation, such as, for example, those derived from breast, prostate, brain, pancreas, liver, bone, and other tissues.

The contacting of the transformed cells to be inhibited with the active ingredient of the present invention can be implemented in vitro using methods well known in the art. For example, the active ingredient can be added directly to the medium in which the subject cells are in culture, either alone or after being combined with a suitable carrier, e.g., a buffer or solvent.

Such contacting of cells in an animal can be implemented in vivo using yet other techniques, also well known in the art. For example, the active ingredient can be mixed with other active or inactive ingredients to form a pharmaceutical composition useful for administration to animals, including humans and other mammals, in amounts as specified above. Such compositions, useful for various avenues of administration of the inventive composition, are discussed further below.

One skilled in the art will appreciate that the present inventive method may be practiced in an animal by any suitable method. In other words, a variety of ways are available of administering a compound useful in the method of the present invention to a mammal, for example, for the inhibition of transformed cells in vivo. Although more than one route can be used to administer a particular compound, a particular route can provide a more immediate and more effective reaction than another route. Accordingly, the described methods are merely exemplary and are in no way limiting.

The dose administered to an animal, particularly a human, in accordance with the present invention should be sufficient to effect the desired response, i.e., inhibition of transformed cells, in the animal over a reasonable time frame. One skilled in the art will recognize that dosage will depend upon a variety of factors, including the age, species, condition or disease state, and body weight of the animal, as well as the amount and kind of transformed cells or tissue present in the animal. The size of the dose will also be determined by the route, timing and frequency of administration as well as the existence, nature, and extent of any adverse side-effects that might accompany the administration of a particular compound and the desired physiological effect. It will be appreciated by one of skill in the art that various conditions or disease states, in particular the specific transformed cell type to be inhibited, may require prolonged treatment involving multiple administrations. It should be noted that the bischloromethyl compound was not toxic in an animal when administered in five consecutive daily doses of 250 mg/kg body mass.

Suitable doses and dosage regimens can be determined by conventional range-finding techniques known to those of ordinary skill in the art. Generally, treatment is initiated with smaller dosages that are less than the optimum dose of the compound. Thereafter, the dosage is increased by small increments until the optimum effect under the circumstances is reached. The present inventive method typically will involve the administration of about 0.1 to about 300 mg or more of one or more of the compounds described above per kg body weight of the animal. Indeed, one of the most surprising aspects of the present invention is the degree to which it is nontoxic at high doses (e.g., 250 mg/kg) to a mammal. Such high doses are useful for chemotherapeutic treatment, whereby transformed cells are inhibited and preferably killed within such a treated mammal.

The present invention also provides a pharmaceutical composition comprising a pharmaceutically acceptable carrier and an amount of the active ingredient sufficient to inhibit or stop the growth of transformed cells while leaving normal cells unimpaired or only slightly impaired. The carrier may be any of those conventionally used and is limited only by physico-chemical considerations, such as solubility and lack of reactivity with the compound, and by the route of administration. It will be appreciated by one of ordinary skill in the art that, in addition to the following described pharmaceutical composition, the compounds of the present inventive method may be formulated as inclusion complexes, such as cyclodextrin inclusion complexes, or liposomes.

The present invention thus provides a pharmaceutical composition for inhibiting transformed cells in an animal comprising: (a) an effective amount of at least one of the group consisting of 2,9-bis(halomethyl)-1,10-phenanthroline and structural congeners thereof, and (b) a pharmaceutically acceptable carrier. The pharmaceutical composition will typically comprise at least about 7 mg of the active ingredient or ingredients per dose, presuming an average animal body mass of 70 kg. A preferred formulation of the pharmaceutical composition comprises from about 7 mg to about 70 grams of the active ingredient per dose. More preferably, the pharmaceutical composition comprises from about 70 mg to about 35 grams of the active ingredient per dose. Most preferably, the pharmaceutical composition comprises from about 8 grams to about 15 grams of the active ingredient per dose.

The compound used in the pharmaceutical composition is preferably 2,9-bis(chloromethyl)-1,10-phenanthroline or 2,9-bis(bromomethyl)-1,10-phenanthroline; more preferably, the compound used in the pharmaceutical composition is 2,9-bis(chloromethyl)-1,10-phenanthroline.

When the active ingredient used is the chloromethyl phenanthroline derivative, the pharmaceutical composition will typically comprise at least about 7 mg of the active ingredient; more preferably, such a composition comprises from about 7 mg to about 70 grams of the active ingredient;

most preferably, such a composition comprises from about 70 mg to about 35 grams of the active ingredient. Another preferred composition comprises from about 70 mg to about 1 gram of the chloromethyl phenanthroline derivative. When the active ingredient used is the bromomethyl phenanthroline derivative, the pharmaceutical composition will typically comprise at least about 7 mg of the active ingredient; more preferably, such a composition comprises from about 7 mg to about 7 grams of the active ingredient; most preferably, such a composition comprises from about 70 mg to about 3.5 grams of the active ingredient.

Pharmaceutically acceptable acid addition salts may be used in the present invention. Such salts for use in the present inventive pharmaceutical composition include, for example, those derived from mineral acids, such as hydrochloric, hydrobromic, phosphoric, metaphosphoric, nitric and sulfuric acids, and organic acids, such as tartaric, acetic, citric, malic, lactic, fumaric, benzoic, glycolic, gluconic, succinic, p-toluenesulphonic acids, and arylsulphonic.

The pharmaceutically acceptable excipients described herein, for example, vehicles, adjuvants, carriers or diluents, are well-known to those who are skilled in the art and are readily available to the public. It is preferred that the pharmaceutically acceptable carrier be one that is chemically inert to the active compounds and one that has no detrimental side effects or toxicity under the conditions of use.

The choice of excipient will be determined in part by the particular phenanthroline derivative, as well as by the particular method used to administer the composition. Accordingly, there is a wide variety of suitable formulations of the pharmaceutical composition of the present invention. The following formulations for oral, aerosol, parenteral, subcutaneous, intravenous, intramuscular, interperitoneal, rectal, and vaginal administration are merely exemplary and are in no way limiting.

Injectable formulations are among those formulations that are preferred in accordance with the present inventive methods. The requirements for effective pharmaceutical carriers for injectable compositions are well known to those of ordinary skill in the art. See *Pharmaceutics and Pharmacy Practice*, J. B. Lippincott Company, Philadelphia, Pa., Banker and Chalmers, eds., pages 238–250, (1982), and *ASHP Handbook on Injectable Drugs*, Toissel, 4th ed., pages 622–630 (1986). It is preferred that such injectable compositions be administered intravenously.

Topical formulations are well-known to those of skill in the art and are suitable in the context of the present invention for application to skin as therapy for certain skin cancers.

Formulations suitable for oral administration can consist of (a) liquid solutions, such as an effective amount of the compound dissolved in diluents, such as water, saline, or orange juice; (b) capsules, sachets, tablets, lozenges, and troches, each containing a predetermined amount of the active ingredient, as solids or granules; (c) powders; (d) suspensions in an appropriate liquid; and (e) suitable emulsions. Liquid formulations may include diluents, such as water and alcohols, for example, ethanol, benzyl alcohol, and the polyethylene alcohols, either with or without the addition of a pharmaceutically acceptable surfactant, suspending agent, or emulsifying agent. Capsule forms can be of the ordinary hard- or soft-shelled gelatin type containing, for example, surfactants, lubricants, and inert fillers, such as lactose, sucrose, calcium phosphate, and corn starch. Tablet forms can include one or more of lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and pharmacologically compatible excipients. Lozenge forms can comprise the active ingredient in a flavor, usually sucrose and acacia or tragacanth, as well as pastilles comprising the active ingredient in an inert base, such as gelatin and glycerin, or sucrose and acacia, emulsions, gels, and the like containing, in addition to the active ingredient, such excipients as are known in the art.

The active ingredients of the present invention, alone or in combination with other suitable components, can be made into aerosol formulations to be administered via inhalation. These aerosol formulations can be placed into acceptable pressurized propellants, such as dichlorodifluoromethane, propane, nitrogen, and the like. They also may be formulated as pharmaceuticals for non-pressured preparations, such as in a nebulizer or an atomizer. Such spray formulations may be used to spray mucosa.

Formulations suitable for parenteral administration include aqueous and non-aqueous, isotonic sterile injection solutions. Such solutions can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The compound may be administered in a physiologically acceptable diluent in a pharmaceutical carrier, such as a sterile liquid or mixture of liquids, including water, saline, aqueous dextrose and related sugar solutions, an alcohol, such as ethanol, isopropanol, or hexadecyl alcohol, glycols, such as propylene glycol or polyethylene glycol, dimethylsulfoxide, glycerol ketals, such as 2,2-dimethyl-1,3-dioxolane-4-methanol, ethers, such as poly(ethyleneglycol) 400, an oil, a fatty acid, a fatty acid ester or glyceride, or an acetylated fatty acid glyceride with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils useful in parenteral formulations include petroleum, animal, vegetable, or synthetic oils. Specific examples of oils useful in such formulations include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters.

Suitable soaps for use in parenteral formulations include fatty alkali metal, ammonium, and triethanolamine salts, and suitable detergents include (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylenepolypropylene copolymers, (d) amphoteric detergents such as, for example, alkyl-β-aminopropionates, and 2-alkylimidazoline quaternary ammonium salts, and (e) mixtures thereof.

The parenteral formulations typically will contain from about 0.5 to about 25% by weight of the active ingredient in solution. Preservatives and buffers may also present in such formulations. In order to minimize or eliminate irritation at the site of injection, such compositions preferably contain one or more nonionic surfactants having a hydrophile-lipophile balance (HLB) of from about 12 to about 17. The quantity of surfactant in such formulations will typically range from about 5 to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol. The parenteral formulations can be presented in unit-dose or multi-dose sealed containers, such as ampules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets of the kind previously described.

Additionally, the active ingredients useful in the present inventive method can be made into suppositories by mixing with a variety of bases, such as emulsifying bases or water-soluble bases. Formulations suitable for vaginal administration may be presented as pessaries, tampons, creams, gels, pastes, foams, or spray formulas containing, in addition to the active ingredient, such carriers as are known in the art to be appropriate.

The following examples further illustrate the present invention and, of course, should not be construed as in any way limiting its scope.

EXAMPLE 1

This example illustrates the cytotoxicity of a phenanthroline derivative, namely 2,9-dimethyl1,10-phenanthroline (2,9-DMP), which is structurally similar to the phenanthroline derivatives useful in the context of the present invention.

The phenanthroline derivative 2,9-DMP was added to a culture of mouse L1210 leukemia cells alone (o), with copper sulfate (●), and with copper sulfate and bathocuproine sulfonate (□). The concentrations of copper sulfate and bathocuproine sulfonate used in these experiments were both 25 µM. Methods used to grow the cells and to administer the test compounds were standard methods, well known to ordinary practitioners. The growth of the cells as a percent of control was determined, and the results were plotted in the graph of FIG. 1.

As is apparent from the depicted results, 2,9-DMP is somewhat effective in the inhibition of transformed cells, with cell growth falling to less than about 20% of control at concentrations above about 0.4 µM. The cytotoxic effectiveness of 2,9-DMP was improved by added copper ion such that cell growth fell to less than about 20% of control at concentrations above about 0.1 µM and to less than about 10% of control at concentrations above about 0.4 µM. In contrast, the cytotoxicity of 2,9-DMP, and thus its ability to inhibit cell growth, was prevented by addition of bathocuproine sulfonate (BCS), even in the presence of copper ion.

This example demonstrates the need of the presence of copper in rendering 2,9-DMP effective in the inhibition of transformed cell growth. Because BCS is a copper chelator, its alleviation of the cytotoxicity of 2,9-DMP indicates that the cytotoxicity of 2,9-DMP is copper dependent. See Mohindru et al., Nature, 303, 64–65 (1983).

EXAMPLE 2

This example illustrates the cytotoxicity of other phenanthroline derivative compounds, namely 2-bromomethyl-9-methyl-1,10-phenanthroline (2-BM-9-MP) and 2-chloromethyl-9-methyl-1,10-phenanthroline (2-CM-9-MP). These derivatives are structurally similar to the phenanthroline derivatives useful in the context of the present invention, except they have a single halo substitution as opposed to the double halo substitution on the compounds that are useful in the context of the present invention.

The aforementioned monohalomethyl compounds were prepared and characterized as described by Newkome et al., J. Org. Chem., 54, 1766–1769 (1989). The compounds were then added to different cultures of mouse L1210 leukemia cells alone (o), with copper sulfate (□), with BCS (●), or with BCS and copper sulfate (■). The concentrations of copper and BCS used in these experiments were 10 µM and 100 µM, respectively. Methods used to grow the cells and to administer the test compounds were standard methods, well known to ordinary practitioners, and were similar to those used in Example 1. The growth of the cells as a percent of controls were determined, and the results were plotted in the graph of FIG. 2.

The results indicate that the inhibitory activity of both the monobromomethyl (left-hand graph) and monochloromethyl (right-hand graph) phenanthroline derivatives were less than that of the unhalogenated parent compound of Example 1. For example, nearly 3 µM of the copper-chelated monobrominated phenanthroline was required to inhibit cellular growth to 20% of control, whereas less than one-tenth of that concentration of the copper chelated parent compound inhibited to the same level.

Figure 2:
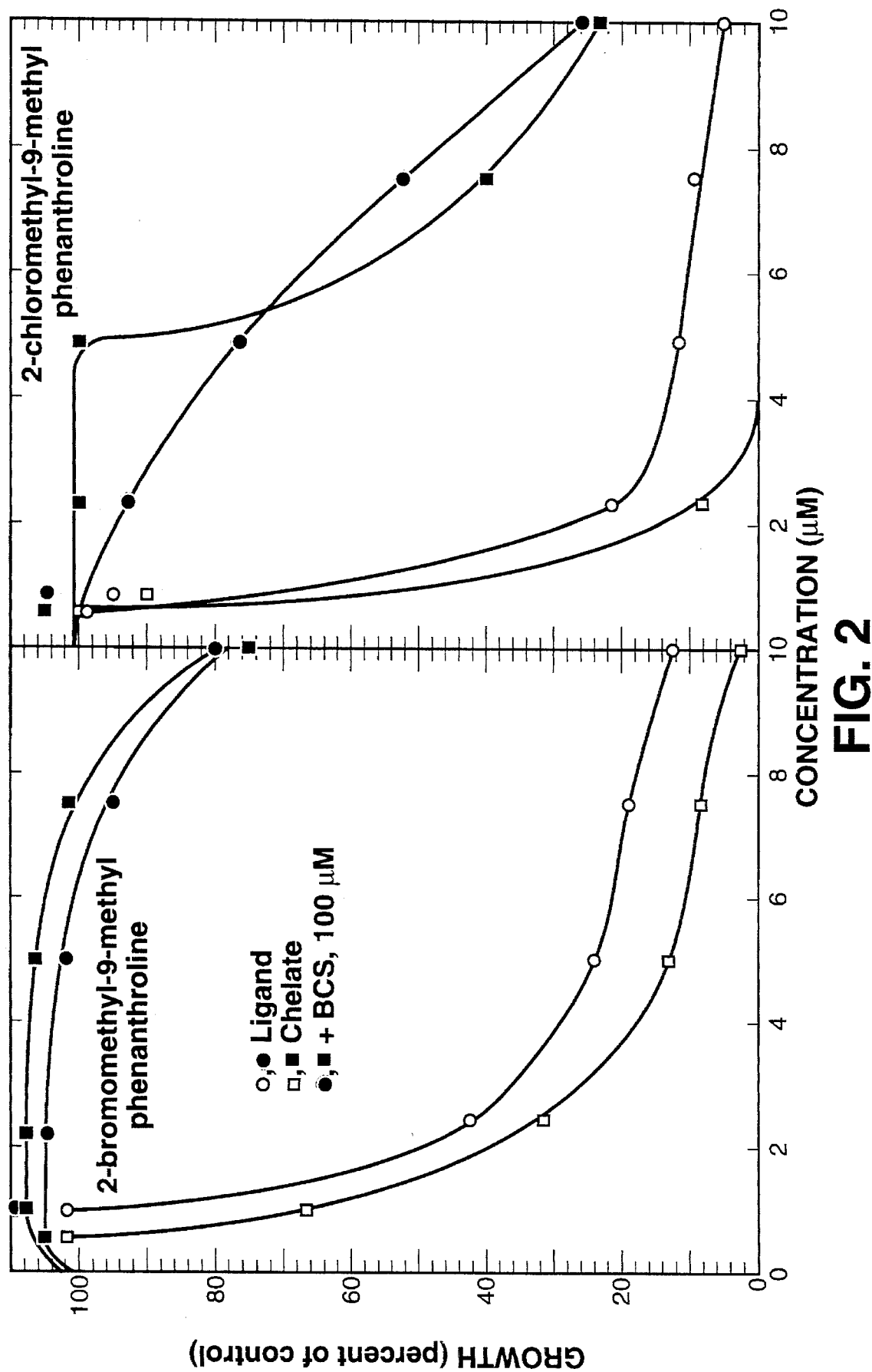
FIG. 2 is a graph that illustrates the inhibition of growth of murine L1210 leukemia cells in culture when incubated in the presence of varying concentrations of (1) 2-bromomethyl-9-methyl-1,10-phenanthroline or 2-chloromethyl-9-methyl-1,10-phenanthroline (o); (2) the same compounds in the presence of copper (□); and (3) the same compounds in the presence of bathocuproine disulfonate alone or copper and bathocuproine disulfonate (■ or ●, respectively).

This example further demonstrates the need of copper in rendering the monohalogenated phenanthroline derivative effective in the inhibition of the growth of transformed cells. As with the unhalogenated phenanthroline derivative of Example 1, the presence of copper increased, and the presence of BCS reduced, the inhibitory effect of the monohalogenated phenanthroline derivatives, as illustrated in FIG. 2. In view of the potential toxic impact of copper alone, however, the requirement of copper to potentiate the cytotoxic effect of the monohalomethyl phenanthroline derivatives, as well as the unhalogenated phenanthroline derivatives, makes these compounds less desirable.

EXAMPLE 3

This example illustrates the cytotoxicity of bis(halomethyl)phenanthroline compounds as used in the present invention. These bis(halomethyl)phenanthroline derivatives, despite displaying structural similarities to the compounds tested in Examples 1 and 2, display copper-independence and cytotoxicity at low levels.

Bis(halomethyl)phenanthroline compounds were synthesized according to the method of Newkome et al., J. Org. Chem., 48, 5112–5114 (1983). Such compounds, namely, 2,9-bis(bromomethyl)phenanthroline and 2,9-bis(chloromethyl)phenanthroline, were added in the presence of copper, but with or without BCS (the copper chelator shown in Examples 1 and 2 to reduce inhibitory activity), to the culture media of L1210 mouse cells, using the same methods of Examples 1 and 2. The concentrations of copper and BCS used in these experiments were 10 µM and 100 µM, respectively. The growth of the cells as a percent of control were determined, and the results plotted in the graph of FIG. 3, wherein open squares (□) represent the compound plus copper chelate and solid squares (■) represent the compound together with both copper and BCS addition to the culture medium.

Figure 3:
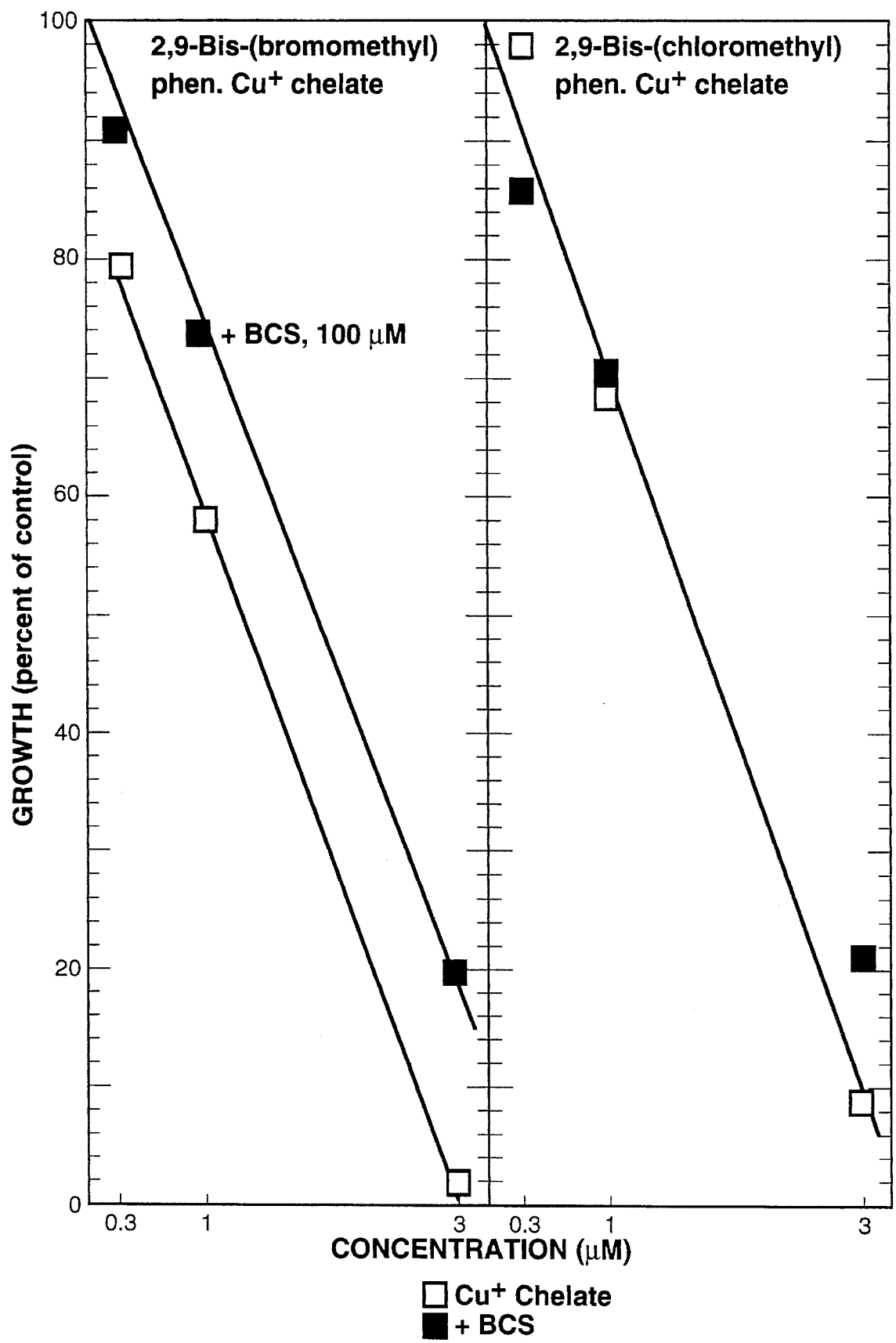
FIG. 3 is a graph that illustrates the inhibition of growth of the murine L1210 leukemia cells in culture when incubated in the presence of varying concentrations of 2,9-bis(bromomethyl)-1,10-phenanthroline or 2,9-bis(chloromethyl)-1,10-phenanthroline, either as a copper chelate (□) or in the presence of bathocuproine disulfonate (■).

As is apparent from the graph of FIG. 3, the inhibitory effect of both bis(halomethyl) phenanthroline compounds was substantially independent of the presence of available copper, as demonstrated by the near similarity of the growth versus concentration curves in the presence and absence of BCS. For example, the brominated derivative showed a greater inhibitory effect in the presence of copper by only about 10% as compared to the same compound in the absence of available copper (i.e., in the presence of BCS). The chlorinated derivative showed less variability relative to the availability of copper, although at the highest concentration of active ingredient tested (3 μM), the same 10% difference was noted between the copper-chelated and the unchelated phenanthroline derivative. Also shown in FIG. 3 is that the cytotoxicities of the two bis(halomethyl)phenanthroline compounds were approximately equal in culture, about 3 μM of either phenanthroline derivative in the absence of copper (i.e., in the presence of BCS) resulted in at most only 20–22% of the growth exhibited by control cells and in the presence of copper resulted in 2–10% of the growth exhibited by control cells.

EXAMPLE 4

This example illustrates the toxicity of the bis(halomethyl)phenanthroline compounds used in the context of the present invention in whole animals.

Laboratory mice were injected intraperitoneally with the bis(chloromethyl)phenanthroline compound at a dosage of 240 mg/kg of body mass in five consecutive days, and displayed no toxic effects, i.e., none of the experimental animals died or displayed any deleterious effects. Another set of mice were treated similarly with the bis(bromomethyl)phenanthroline derivative; all died when given a dose of 60 mg/kg of body mass. Accordingly, the bis(chloromethyl)phenanthroline is better tolerated by mammals, although the level of toxicity exhibited by the brominated derivative would not conclusively contraindicate its use. These toxicity data were provided by The Developmental Therapeutics Program of the National Cancer Institute.

With reference to bis(chloromethyl)phenanthroline, the tolerated injected quantity of 240 mg/kg of body mass can be converted to an approximate concentration in an animal, in view of the molecular weight of the compound (277 daltons) and the rough equivalent between a liter of water and a kg of body mass. Accordingly, the equivalent concentration of the active ingredient in vivo is 866 μM. This value of tolerated in vivo concentration of bis(chloromethyl)phenanthroline is compared to the in vitro results presented in Example 5.

EXAMPLE 5

This example illustrates the ability of bis(chloromethyl)phenanthroline used in the context of the present invention to inhibit and reverse the growth of various human transformed cell lines.

A dose response study of the growth of various human tumor cell lines was generated using standard culture methods known in the art; the data were collected by The Developmental Therapeutics Program of the National Cancer Institute. The results, provided in the following table, indicate that nearly all transformed cells cease growth in the presence of micromolar concentrations of the bis(chloromethyl)phenanthroline. The table provides the names of the various human transformed cell lines tested and the concentrations of bis(chloromethyl)phenanthroline required to effect, relative to controls, 50% growth, no growth, and 50% kill of the transformed cells subjected to exposure to the bis(chloromethyl)phenanthroline in accordance with the present invention. As can be seen, the majority of cell lines required, on average, only about a 5.66 μM concentration of the phenanthroline derivative to preclude growth of the transformed cells in vitro. Indeed, 70% of the cell lines were shown not only to experience precluded growth, but cell death, when exposed to less then 100 μM of the active ingredient. As demonstrated in Example 4, an animal is apparently tolerant of at least 8.5 times that concentration, which clearly selects against transformed cells.

Accordingly, this example demonstrates that bis(chloromethyl)phenanthroline, the preferred compound used in the context of the present invention, is capable of inhibiting the growth of transformed cells at levels that represent no substantial toxic effect to animals when transformed cells contained therein are inhibited by administration of the active ingredient in vivo.

| CELL LINE | Concentration of bis(chloromethyl)-phenanthroline (in μM) | | |
|---|---|---|---|
| | 50% Growth | No Growth | 50% Loss |
| | (Relative to Control) | | |
| LEUKEMIA | | | |
| CCRF-CEM | 1.80 | 8.64 | >100 |
| HL-60 (TB) | 1.80 | 4.43 | 23.0 |
| K-562 | 3.19 | >100 | >100 |
| MOLT-4 | 1.73 | 4.02 | 9.34 |
| RPMT-8226 | 1.25 | 36.6 | >100 |
| NON-SMALL CELL LUNG CANCER | | | |
| A549/ATCC | 5.14 | >100 | >100 |
| EKVX | 28.1 | >100 | >100 |
| HOP-18 | 3.02 | 9.71 | 31.2 |
| HOP-62 | 2.29 | 5.30 | 19.2 |
| NCI-H226 | 3.06 | 9.91 | 68.3 |
| NCI-H23 | 1.87 | 3.68 | 7.24 |
| NCI-H322M | 2.84 | 8.41 | 29.2 |
| NCI-H522 | 1.76 | 3.44 | 6.71 |
| SMALL CELL LUNG CANCER | | | |
| DMS 114 | 1.62 | 3.53 | 7.72 |
| DMS 273 | 2.84 | >100 | >100 |
| COLON CANCER | | | |
| COLO 205 | 1.56 | 2.94 | 5.54 |
| DLD-A | 1.48 | 2.91 | 5.72 |
| HCC-2998 | 1.56 | 3.11 | 6.18 |
| HCT-116 | 1.80 | 3.87 | 8.31 |
| HCT-15 | 1.95 | 6.47 | >100 |
| HT29 | 1.31 | 2.68 | 5.48 |
| KM12 | 0.761 | 2.39 | 6.43 |
| KM20L2 | 2.72 | 7.21 | 28.3 |
| SW-620 | 3.18 | 14.1 | >100 |
| CNS CANCER | | | |
| SF-268 | 1.79 | 3.74 | — |
| SF-539 | 2.99 | 11.2 | 41.8 |
| SNB-75 | 1.72 | 4.53 | 15.5 |
| SNB-78 | 2.30 | 6.40 | >100 |
| U251 | 2.06 | 4.09 | 8.11 |
| XF 498 | 1.72 | 5.63 | >100 |
| MELANOMA | | | |
| MALME-3M | 1.89 | 3.41 | 6.16 |
| M19-MEL | 1.31 | 2.63 | 5.28 |
| SK-MEL-2 | 1.77 | 4.81 | 16.6 |
| SK-MEL-28 | 1.35 | 2.97 | 6.50 |
| SK-MEL-5 | 1.59 | 3.88 | 9.45 |
| UACC-257 | 0.780 | 2.03 | 5.58 |

-continued

| CELL LINE | Concentration of bis(chloromethyl)-phenanthroline (in μM) | | |
|---|---|---|---|
| | 50% Growth | No Growth | 50% Loss |
| | (Relative to Control) | | |
| UACC-62 | 1.18 | 2.45 | 5.07 |
| OVARIAN CANCER | | | |
| IGROVI | 1.51 | 3.07 | 6.25 |
| OVCAR-3 | 1.75 | 4.93 | 18.4 |
| OVCAR-4 | 3.15 | 9.37 | 34.9 |
| OVCAR-5 | 1.87 | 3.52 | 6.63 |
| OVCAR-8 | 6.85 | >100 | >100 |
| SK-OV-3 | 8.90 | >10.0 | >10.0 |
| RENAL CANCER | | | |
| RXF-393 | 1.65 | 3.16 | 6.03 |
| SN12C | 3.35 | >100 | >100 |
| UO-31 | 1.69 | 3.21 | 6.08 |
| MISCELLANEOUS | | | |
| MCF7 | 0.564 | 2.48 | 8.88 |
| MCF7/ADR-RES | 1.93 | 4.48 | >100 |
| P388 | 0.735 | 3.01 | 25.1 |
| P388/ADR | 0.355 | 3.82 | >100 |

All of the references cited herein, including publications, patents, and patent applications, are hereby incorporated in their entireties by reference.

While this invention has been described with an emphasis upon preferred embodiments, it will be obvious to those of ordinary skill in the art that variations of the preferred embodiments may be used and that it is intended that the invention may be practiced otherwise than as specifically described herein. Accordingly, this invention includes all modifications encompassed within the spirit and scope of the invention as defined by the following claims.

What is claimed is:

1. A method of inhibiting cancer cells, which method comprises contacting cancer cells with an inhibiting concentration or amount of at least one compound of the group consisting of 2,9-bis(halomethyl)- 1,10-phenanthrolines, wherein said cancer cells are sensitive to said compound.

2. The method of claim 1, wherein said cancer cells are selected from the group consisting of lung, colon, ovary, skin, blood, central nervous system, and kidney cancer cells.

3. The method of claim 2, wherein said cancer cells are selected from the group consisting of colon, skin, central nervous system, and kidney cancer cells.

4. The method of claim 3, wherein said cancer cells are colon cancer cells.

5. The method of claim 1, wherein said cancer cells are selected from the group consisting of breast, prostate, brain, pancreas, liver, and bone cancer cells.

6. The method of claim 5, wherein said cancer cells are breast cancer cells.

7. The method of claim 1, wherein said cancer cells are renal cancer cells.

8. The method of claim 1, wherein said cancer cells are melanoma cells.

9. The method of claim 1, wherein said compound is 2,9-bis(bromomethyl)-1,10-phenanthroline.

10. The method of claim 1, wherein said compound is 2,9-bis(chloromethyl)-1,10-phenanthroline.

11. The method of claim 9, wherein said contacting occurs in vitro.

12. The method of claim 11, wherein said concentration is at least about 0.1 micromolar.

13. The method of claim 12, wherein said concentration is from about 0.1 micromolar to about 200 micromolar.

14. The method of claim 9, wherein said contacting occurs in an animal.

15. The method of claim 14, wherein said amount is at least about 0.1 mg per kg of body mass of the animal.

16. The method of claim 15, wherein said amount is from about 0.1 mg to about 50 mg per kg of body mass of the animal.

17. The method of claim 16, wherein said amount is from about 1 mg to about 40 mg per kg of body mass of the animal.

18. The method of claim 10, wherein said contacting occurs in vitro.

19. The method of claim 18, wherein said concentration is at least about 1 micromolar.

20. The method of claim 19, wherein said concentration is from about 1 micromolar to about 800 micromolar.

21. The method of claim 20, wherein said concentration is from about 2 micromolar to about 150 micromolar.

22. The method of claim 10, wherein said contacting occurs in an animal.

23. The method of claim 22, wherein said amount is at least about 1 mg per kg of body mass of the animal.

24. The method of claim 23, wherein said amount is from about 1 mg to about 1000 mg per kg of body mass of the animal.

25. The method of claim 24, wherein said amount is from about 10 mg to about 500 mg per kg of body mass of the animal.

26. The method of claim 1, wherein said contacting occurs in vitro.

27. The method of claim 1, wherein said contacting occurs in an animal.

* * * * *